(12) United States Patent
Fischer et al.

(10) Patent No.: US 8,308,718 B2
(45) Date of Patent: Nov. 13, 2012

(54) CRYOSURGICAL INSTRUMENT FOR SEPARATING A TISSUE SAMPLE FROM SURROUNDING TISSUE OF A BIOLOGICAL TISSUE THAT IS TO BE TREATED

(75) Inventors: Klaus Fischer, Nagold (DE); Matthias Voigtländer, Gomaringen (DE); Daniel Schäller, Tübingen (DE); Mara Szyrach, Tübingen (DE); Irina Sigle, Mössingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 670 days.

(21) Appl. No.: 12/520,122

(22) PCT Filed: Dec. 11, 2007

(86) PCT No.: PCT/EP2007/010822
§ 371 (c)(1),
(2), (4) Date: Jun. 19, 2009

(87) PCT Pub. No.: WO2008/074422
PCT Pub. Date: Jun. 26, 2008

(65) Prior Publication Data
US 2010/0016847 A1    Jan. 21, 2010

(30) Foreign Application Priority Data

Dec. 19, 2006  (DE) .......................... 10 2006 059 999
May 2, 2007    (DE) .......................... 10 2007 020 582

(51) Int. Cl.
*A61B 18/02*    (2006.01)

(52) U.S. Cl. ........................................................ 606/21
(58) Field of Classification Search ............... 606/20–26
See application file for complete search history.

(56) References Cited

U.S. PATENT DOCUMENTS

| | | | |
|---|---|---|---|
| 6,032,675 A | 3/2000 | Rubinsky | |
| 6,401,722 B1* | 6/2002 | Krag .............................. | 128/898 |
| 2003/0093088 A1* | 5/2003 | Long et al. ..................... | 606/129 |
| 2003/0181896 A1 | 9/2003 | Zvuloni et al. | |
| 2003/0195436 A1 | 10/2003 | Van Bladel et al. | |
| 2007/0055173 A1* | 3/2007 | DeLonzor et al. ............. | 600/564 |

FOREIGN PATENT DOCUMENTS

| | | |
|---|---|---|
| DE | 2326987 | 12/1974 |
| EP | 1296607 | 9/2005 |
| WO | WO 01/67975 | 9/2001 |
| WO | WO 01/97702 | 12/2001 |

\* cited by examiner

*Primary Examiner* — Michael Peffley
*Assistant Examiner* — Daniel Fowler
(74) *Attorney, Agent, or Firm* — Dickstein Shapiro LLP

(57) ABSTRACT

A cryosurgical instrument and a method for separating a tissue sample from surrounding tissue of a biological tissue that is to be treated. The cryosurgical instrument includes a probe for guiding a probe head on to a biological tissue to be treated, and gas conduits for delivering coolant gas. The probe head is designed so that, in order to collect a tissue sample, a limited region of the tissue is cooled by means of the gas delivered and is separated from the surrounding tissue in a state in which it is frozen on the probe head. The instrument includes a support tube or hose in which the probe is guided and which can be moved relative to the probe in such a way that the surrounding tissue can be counter-supported during separation of the tissue sample.

19 Claims, 3 Drawing Sheets

CRYOSURGICAL INSTRUMENT FOR SEPARATING A TISSUE SAMPLE FROM SURROUNDING TISSUE OF A BIOLOGICAL TISSUE THAT IS TO BE TREATED

BACKGROUND

The invention relates to a cryosurgical instrument and a method for separating a tissue sample from surrounding tissue of a biological tissue to be treated.

In cryosurgery, targeted controlled use of low temperatures are employed for devitalizing biological tissue. With flexible probes in particular, cryosurgery can be employed to remove foreign bodies from body cavities by freezing them solid to the cryoprobe or to a probe head, for example, foreign bodies which have been accidentally inhaled and must be removed from the respiratory tract. Cryosurgery is also suitable for collection of tissue samples (biopsy). In this context, a tissue sample can be frozen to the probe head and, after separation from the surrounding tissue, made accessible to an investigation.

There are various possibilities for deep-freezing in surgery; one is based on the Joule-Thomson effect: the atoms or molecules of an expanding gas below the inversion temperature counteract mutual attraction, such that the gas loses internal energy and cools. $CO_2$ or $N_2O$ is conventionally employed as the expanding gas. These gases are—referred to as working or coolant gases.

Cryosurgical instruments of the type just described conventionally have a probe which can be brought to the tissue to be treated, and gas conduits which pass through the probe and release working gas into the inner lumen of the probe, where the working gas expands and consequently cools the tips of the probe (the probe head). Since the probe head is generally produced from a thermally conductive material, conduction of the heat of the tissue via the probe head and cooling is consequently ensured.

Tissue samples are usually collected by conventional routes by means of forceps biopsy. However, the specimen obtained is very small and is usually squeezed during removal. Biopsy by means of cryosurgery makes it possible to collect tissue samples considerably more efficiently. For the purpose of a biopsy, the cryoprobe (rigid or flexible) is conventionally guided to the desired place, e.g., in a gastrointestinal tract, via a working channel of an endoscope (which may also be either rigid or flexible). The tip of the probe or probe head is positioned on the tissue to be treated, e.g. a mucous membrane, and a desired region of tissue (the tissue sample) freezes solid on the probe head due to the cooling mechanisms described above. The tissue sample thus adheres to the cooled probe head and the frozen tissue can be detached from the surrounding tissue by a pulling movement.

The detachment requires application of a relatively high force, which must be applied by the user. This presents numerous problems if the tissue to be treated also moves during the separation operation (that is to say during a pulling movement). For example, a high pulling force cannot be exerted on the large intestine (if a biopsy sample is to be obtained from that organ), since the large intestine floats free in the abdomen. The necessary pulling force can be applied here—if at all—only in pulses. Because of this, injuries may occur in the surrounding tissue (from too much force being applied), or a tissue sample cannot be removed at all because the surrounding tissue yields too much. Under such conditions, the frozen tissue sample can prematurely detach from the probe head.

The invention is therefore based on the object of developing a cryosurgical instrument that can reliably remove a tissue sample without damage to the tissue or to the patient. The object of the invention is furthermore to provide a method for separating a tissue sample from surrounding tissue of a biological tissue to be treated, which solves the problems described.

BRIEF DESCRIPTION OF THE DRAWINGS

The invention is described in the following with the aid of embodiment examples which are explained in more detail with the aid of the figures.

SUMMARY OF THE INVENTION

Figure 1:
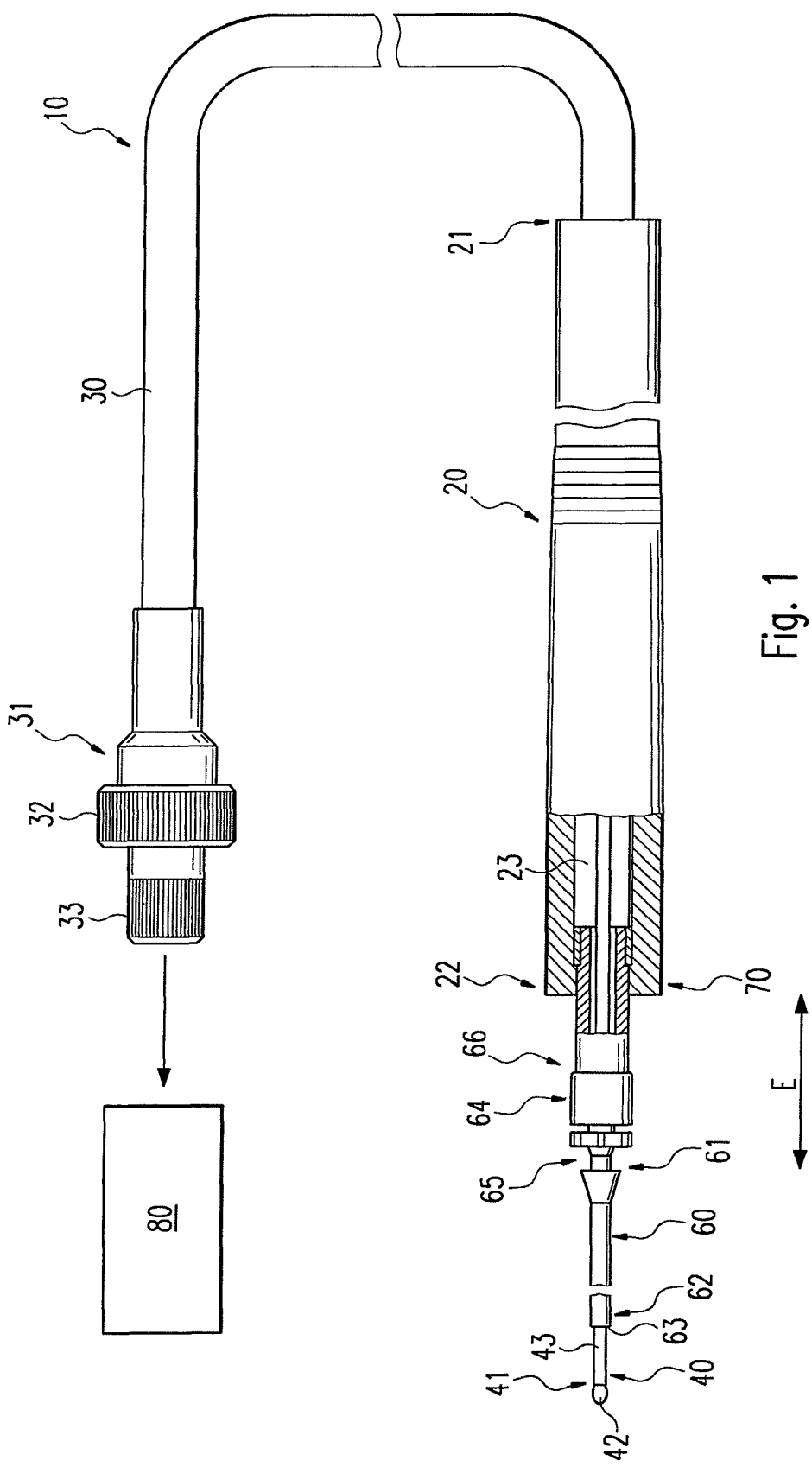
FIG. 1 shows an embodiment of the cryosurgical instrument according to the invention, the instrument being partly shown, in section.

An object of the present invention is achieved by a cryosurgical instrument which comprises a probe for guiding a probe head on to a biological tissue to be treated, and gas conduits for delivering coolant gas from a gas source to the probe head and for removing the coolant gas from the probe head, wherein the probe head is designed in such a way that, in order to collect a tissue sample, a limited region of the tissue can be cooled by means of the gas delivered and can be separated from the surrounding tissue in a state in which it is frozen on the probe head. The instrument has a support means or structure in which the probe is guided and which can be moved relative to the probe in such a way that the surrounding tissue can be supported by means of the support means during separation of the tissue sample.

An important point of the invention lies in the fact that by means of the support means a counter bearing is created, which, during separation of the tissue sample from the surrounding tissue, supports the latter and holds it in position. The probe and support means can be further moved relative to one another in such a way that the support means comes to rest on the tissue surrounding the tissue sample, while the tissue (in principle the biopsy sample) is pulled on via the probe. In other words, the support means and probe can be moved relative to one another in such a way that either the probe head and, where appropriate, parts of a probe body of the probe can be released, or the support means can be moved beyond the probe head. By positioning the support means on the tissue, a force of the support means acts on the surrounding tissue and an equal and opposite pulling force acts by the pull on the frozen tissue via the probe (action and equal and opposite reaction) when the frozen tissue is removed from the surrounding tissue by means of the probe head. The support means thus exerts a counter-force on the tissue, while the tissue part frozen on the probe head is pulled on via the probe. The pulling force therefore acts only on a small area, and not on the entire surrounding tissue. The surrounding tissue can therefore be left essentially in its original position and is not adversely stressed.

In a preferred embodiment, the probe has a rigid or flexible shaft or catheter and can be guided through an instrument channel of a rigid or flexible endoscope to the tissue to be treated. In other words, the probe with the probe body and probe head is preferably designed for endoscopic interventions and can be guided in this manner to an operation region in a simple way.

The instrument preferably has a gripping means (i.e., a gripping structure such as a handle) for handling the probe, a proximal end of the probe being mounted in the gripping means. The gripping means facilitates handling of the instrument.

The gas conduits preferably comprise a gas delivery line running through the probe, so that a hollow space inside the probe or probe body can be filled with gas for cooling the probe head. Since the probe head must be cooled by means of the working gas or coolant gas, the gas conduits are designed in such a way that the coolant gas can be brought into contact with the probe head. For this, for example, a hollow space which can be filled with the coolant gas is arranged in the immediate vicinity of the probe head. The gas thus flows through the gas delivery line within the probe in the direction of the probe head into the hollow space and during this cools (e.g. due to the expansion, as described above) the probe head. The gas delivery line is preferably arranged in such a way that it lies within a gas removal line of the gas conduits which is likewise arranged in the probe, the gas removal line preferably being designed in such a way that it includes the hollow space.

The gas conduits not only comprise the line sections (gas delivery line, gas removal line) within the probe, but in one embodiment lead via the gripping means through a tube means. The tube means can then be connected to the cryosurgical apparatus via a further extension of the gas conduits or directly. The cryosurgical instrument therefore preferably includes the probe with the gripping means and the tube means for connection to the cryosurgical apparatus.

Cryosurgery apparatuses are envisaged for the most diverse intended uses and operate, for example, by the above-mentioned Joule-Thomson effect. It would also be possible to perform cryosurgical interventions by means of liquid nitrogen.

Preferably, the support means is designed in such a way that it encloses the probe in the form of a tube or hose. In other words, the support means is designed as a hose or a tube into which the probe is inserted. The support tube is therefore provided here as an outer probe body. The support means and probe are arranged relative to one another in such a way that they can be moved relative to one another or also against one another. By the moving relative to one another, the probe head can be moved beyond an end of the support means close to the probe head (distal end) and is therefore exposed (so that the probe head can reach the tissue for removal of the tissue sample). Conversely, the support tube can be pushed beyond the probe head and the probe head can be received completely in the support tube (with the tissue sample). The support tube can therefore be pushed against the tissue from which the tissue sample is to be taken to support this after the tissue sample has been deposited on the probe head due to freezing.

In one embodiment, a receiving means (i.e., a receiving structure such as a mount) for receiving or mounting a proximal end of the support means is provided, the receiving means and the gripping means being connected to one another and displaceable with respect to one another by means of a coupling unit. This makes it possible for the probe and support means to be moved relative to one another by the receiving means and gripping means being moved relative to one another. The receiving means and gripping means (and therefore support means and probe) can be displaced relative to one another over a defined path length, it being possible for the path length to be determined, e.g., via correspondingly cooperating stops between the receiving means and gripping means, in other words, in the coupling unit.

As already explained above, the probe is preferably guided in the support means. The probe and support means are therefore arranged, e.g., coaxially with respect to one another, the support means enclosing the probe only up to the receiving means, while the probe can run further through the receiving means into the gripping means.

Preferably, the coupling unit is designed in such a way that a pushing means of the receiving means and a channel region of the gripping means interlock at least in part regions, so that the support means and the probe can be moved relative to one another, by means of a pushing or pulling movement of the gripping means and/or receiving means, along a direction of extension of the probe over the defined path length in such a way that at least the probe head can be received in the support means or can be released from this. The pushing means or structure can be a tube or similar shaped object and is therefore guided with one end in the channel region of the gripping means, so that the pushing means and the gripping means can be moved away from one another and towards one another. In other words, a relative movement between the probe and support means takes place in such a way that the probe fixed to the gripping means (at least with a distal end) can be moved out of the support means fixed to the gripping means, and conversely the support means can be pushed over the probe head to such a distance that it holds back the surrounding tissue while the tissue sample is separated. The pushing means here is preferably tubular in design, so that the probe or probe body can be guided further to the gripping means or into this.

Depending on the dimensions of the support means and working channel of the endoscope, the support means can be arranged in a fixed manner (in principle the support means is clamped) in the working channel in such a way that relative movement between the support means and working channel is possible only with difficulty. In this case the probe would then essentially be moved via the gripping means and pushed in the support tube. The aim can also be to move the support means via the pushing means. In any case, the arrangement is envisioned in such a way that it is a matter of the relative movement between the probe on the gripping means and the support means on the receiving means, it also being possible for the probe and support means both to be movable relative to one another; it must be possible to push the support means beyond the probe head or to receive the probe head in the support means to such a distance during separation of the tissue sample that the tissue can be supported and separation can be carried out. Displaceable mounting of the receiving means in the gripping means makes relative movement possible.

The support means is preferably designed in such a way that the tissue region (the tissue sample) frozen on to the probe head can be received in the support means with the probe head. In other words, in order to be able to receive the biopsy sample in the lumen of the support means (the support tube), the support means must have a sufficiently large lumen. Needless to say, the support means including the probe is to be designed in such a way that it can be inserted without problems in a working channel of an endoscope. The possibility of being able to receive the tissue sample in the support means facilitates recovery of the biopsy sample. The probe can be pulled out of the working channel, the biopsy sample safely contained in the lumen of the support means.

If the support means is designed as a tube, the tissue can be contacted at the distal end of the support means via an opening of the positioning edge enclosing the support means. This positioning edge is preferably blunt in design so that it does not cut into the tissue. Needless to say, when designing the positioning edge it must be ensured that this can be guided through the working channel of the endoscope. Furthermore, a material which can undergo elastic deformation up to a certain degree can be used for the support means. Injury to the surrounding tissue can also be avoided by this means.

The probe head, which is preferably constructed from metal (e.g., high-grade steel), is connected to a probe which is preferably constructed from plastic. A polyether ketone (PEK) or polyether ether ketone (PEEK), is envisaged, for example, as the probe material (material for the probe body). PEEK has a high strength, a good resistance to chemicals and a very good heat resistance. The support means is preferably constructed from perfluoro-(ethylene-propylene) plastic (FEP), polytetrafluoroethylene (PTFE) or a plastic of the like.

The method object is achieved in that in a method for separating a tissue sample from surrounding tissue of a biological tissue to be treated, using a cryosurgical instrument which comprises a probe with a probe head and gas conduits for coolant gas from a gas source of a cryosurgical apparatus with a gas delivery line and gas removal line each running through the probe, to the probe head and away from this, and a support means in which the probe is guided and which can be moved relative to the probe, the following steps are envisioned:

guiding the probe to the tissue to be treated, preferably via a working channel of an endoscope, positioning the probe head on the tissue to be treated, delivering coolant gas to cool the probe head, so that, in order to collect the tissue sample, a limited region of the tissue is cooled and freezes on to the probe head, moving the support means and probe relative to one another in such a way that the tissue sample is separated and the surrounding tissue is supported by means of the support means during separation of the tissue sample, and recovering the tissue sample.

By means of this method, a tissue sample can be removed reliably and with a high degree of safety for the patient, since the support means also holds the tissue from which the tissue sample is to be taken in the corresponding position when a pulling force (for separating the tissue sample) acts on the tissue. As soon as the probe with the support means is guided to the tissue to be treated and the probe head has been positioned on the tissue, the probe head is cooled accordingly, so that the tissue sample is frozen and deposited on the probe head. An activation time of, for example, at most two seconds for the cooling means, avoids undesirable freezing-on also of the positioned support means, or a resulting biopsy sample which would be too large to be able to be received in the support means.

As already mentioned above, the probe and support means can be displaced relative to one another. By displacing the elements relative to one another, the support means is pressed against the tissue to be treated. Preferably, the support means is designed in such a way that the tissue sample is dragged into the lumen of the support means at the same time as the probe head. The tissue sample is separated from the surrounding tissue (the sample tears off). This happens very much more gently than in conventional methods, since the pulling force necessary for separating the tissue sample and the force acting on tissue due to the support means oppose each other.

As soon as the tissue sample has been separated from the surrounding tissue and received in the support means, the tissue sample can be recovered. In other words, the tissue sample, safely contained in the support means, can be pulled out of the working channel by means of the cryosurgical instrument.

Preferred embodiments of the invention emerge from the subclaims.

DETAILED DESCRIPTION OF THE INVENTION

In the following description, the same reference numbers are used for the same parts and parts which have the same action.

FIG. 1 shows an embodiment of the cryosurgical instrument 10 according to the invention. With this instrument for biopsy, tissue samples of biological tissue can be collected in a simple manner. The instrument 10 is designed in such a way that it can be employed in endoscopy. The instrument has a gripping means 20, a probe 40, preferably for insertion into a working channel of an endoscope (not shown here), being provided at a distal end 22 of the gripping device. For this, the probe 40 is rigid or flexible in design and can be used with the corresponding endoscopes. The instrument 10 can in principle also be designed in such a way that it can be used without an endoscope, In other words, directly.

The probe 40 has, in addition to a probe body 43, a probe head 42 at a distal end 41 and is sheathed by a tube (or also hose) designed as a support means 60. The support means 60 is fixed to a receiving means 64, the receiving means 64 being mounted such that it is displaceable with respect to the gripping means 20. The receiving means 64 is arranged on the distal end 22 of the gripping means 20 in such a way that an operator can displace the gripping means 20 and the receiving means 64 relative to one another without problems, in order finally to displace the probe 40 and support means 60 against one another, In other words, relative to one another. The probe 40 passes through the receiving means 64 and is guided in the gripping means 20 and coupled there.

At a proximal end 21 of the gripping means 20 a hose 30 is attached, which in turn has a connection means 31 at a proximal end (in principle the proximal end of the instrument). In the state shown, this is covered by a blind plug 33. After removal of the blind plug 33, the instrument 10 can be connected to a cryosurgical apparatus 80 and to a gas source via a knurled nut 32. At least one gas delivery line 50 (shown in FIG. 2) and at least one gas removal line 52 (shown in FIG. 2) are arranged in the hose 30, so that on the one hand the probe 40 can be supplied with coolant gas or working gas and on the other hand the gas can be removed from this again. The hose 30 itself can also serve as the gas removal line 52. The gas lines pass through the hose 30 and are guided via the gripping means 20 and the probe 40 up to the probe head 42. For this, a coupling means (not shown) mounted in the gripping means 20 is provided, in order to connect the probe 40 to the gas lines coming out of the hose 30.

The cryosurgical instrument 10 is preferably guided via the endoscope to the tissue to be treated, from which a biopsy sample is to be collected, and in particular in such a way that the probe head 42 touches the tissue. By delivery of the coolant gas to the probe head 42 or at least in the vicinity thereof, this can be cooled in such a way that a region of the tissue freezes on to this. The probe head 42 is therefore constructed from thermally conductive material, preferably from metal, in order to make freezing on of the tissue possible. The Joule-Thomson effect is utilized for cooling the probe head, i.e. cooling of a real gas under throttled expansion. The gas is therefore only used for cooling the probe head and does not come into contact with the tissue. The tissue frozen on can now be separated from surrounding regions of tissue. The support means 60 facilitates this separation operation. Conventionally, the tissue frozen on to the probe head 42 would have had to be torn off from the remaining tissue by jerking, for example by pulling the probe 40 back from the tissue by jerking. Application of a high force is therefore required when detaching the frozen specimen, e.g. a mucous membrane. This presents problems if the tissue to be treated also moves during the separation operation (during a pulling movement). In this case a high pulling force cannot be exerted on, for example, a large intestine (if a biopsy sample is to be obtained from this), since the large intestine floats free in the abdomen.

To counteract these problems, the cryosurgical instrument 10 according to the invention has the abovementioned support means 60. This is designed such that it acts or can be utilized as a counter bearing during separation of the biopsy specimen from the surrounding tissue. The instrument 10 is designed in principle such that after freezing of the tissue on to the probe head 42, the support tube 60 can be moved, by the cooperation of the gripping means 20 and receiving means 64, relative to the probe 40 in the distal direction, In other words, in the direction of the tissue, in such a way until it lies or is positioned on the tissue (surrounding the actual biopsy specimen). By the movement of the probe 40 and support means 60 or support tube relative to one another, the probe head 42 can be received in the support means 60, so that the biopsy specimen is thereby separated from the surrounding tissue. In other words, the probe head 42 must have dimensions such that the support means 60 can be pushed over this. Only in this way can separation of the tissue sample be effected by the pulling movement on the tissue. By positioning a distal end 62 of the support tube 60 with the edge (positioning edge) 63 enclosing the opening of the tube on the tissue, the force of the support tube (In other words, the support means) 60 acts on the tissue surrounding the biopsy sample and is equal and opposite to the pulling force for separating the frozen tissue (action and equal and opposite reaction). The pulling force on the tissue for "tearing off" the tissue sample is now moderated by the support means on the tissue surrounding the tissue sample. The surrounding tissue can therefore be left essentially in its original position and is not adversely stressed. In all cases the probe 40 and support means 60 can therefore be moved relative to one another in such a way that the surrounding tissue can be supported by means of the support means 60 during separation of the tissue sample, the tissue sample frozen on to the probe head being received into the support tube.

Since the support means 60 simultaneously serves as a means for recovering the biopsy specimen, the tissue sample received in the support means can be removed from the working channel 90 under protection with the probe 40.

As shown further in FIG. 1, the receiving means 64 comprises a holding means 65 in which the support means 60 is received (e.g. clamped or screwed) with a proximal end 61. In this embodiment example, the support means 60 therefore encloses the probe 40 only up to the receiving means 64, while the probe 40 is guided further in the gripping means 20 without this casing. The receiving means 64 furthermore comprises a pushing means 66, to which the holding means 65 is connected, e.g. screwed or clamped. The pushing means 66 is guided in the gripping means 20 in a channel region 23 of the gripping means 20, so that the probe 40 and support means 60 can be moved relative to one another in the direction E, that of the extension of the probe, as already described above. The pushing means 66 and channel region 23 form a coupling unit 70. The pushing means 66 abuts, for example, with corresponding regions on stops formed by the gripping means 20, in order to limit or to define the displacement path of the pushing means 66 in this way and to retain the pushing means 66 in the gripping means 20 or in the channel region 23. The elements for mounting the probe in the gripping means can also form path-limiting stops. In this embodiment example, the pushing means 66 is designed in a tubular form with a channel in such a way that the probe 40 can be guided through the pushing means 66.

In this embodiment example, the pushing means is received in the channel region of the gripping means with an end facing the gripping means, while the opposite end of the pushing means projects out of the gripping means. The gripping means and the pushing means can therefore be grasped by an operator and the two elements can be moved relative to one another, In other words, moved towards one another or away from one another.

The proximal region 61 of the support means 60 can additionally be surrounded by a further hose element (not shown) as protection from kinking, so that the probe with the support means is extremely stable in design in the region of the gripping means and cannot be kinked during use.

Figure 2:
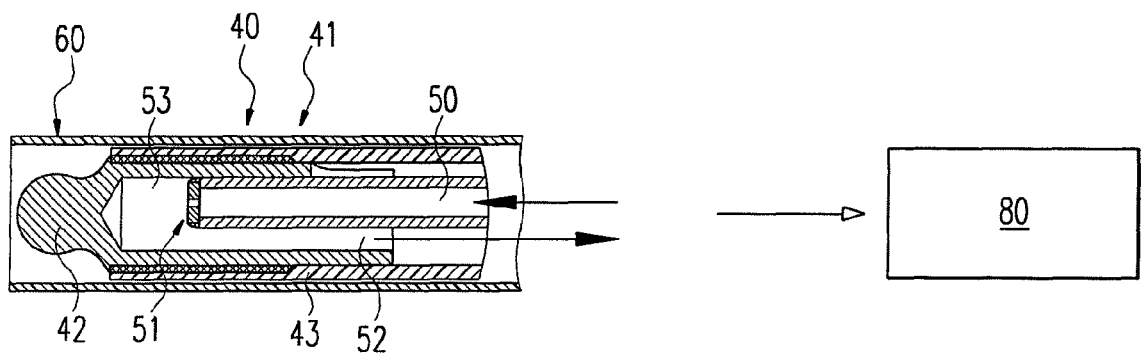
FIG. 2 shows a section of the instrument according to the invention which is connected to a cryosurgery apparatus, with a diagram of gas conduits and the distal end of a probe with the probe head, in section.

FIG. 2 shows a section of the instrument according to the invention which is connected to the cryosurgery apparatus 80, diagrams of the gas conduits 50, 52 in part and the distal end 41 of the probe 40 with the probe body 43 and probe 42 being shown in section. Via the gas source (not shown) connected to the cryosurgery apparatus 80, the working gas for cooling the probe head 42 is led through the gas delivery lines 50 to the probe head 42. The distal end 41 of the probe 40 comprises the probe head 42. The gas lines reach to the probe head 42. In this embodiment example, the gas delivery line 50 of the probe 40 is arranged within the gas removal line 52, the gas removal line 52 having a larger diameter than the gas delivery line 50 for this purpose. The gas delivery line 50 has an aperture 51 at its end close to the probe head, via which the gas enters into a hollow space 53 formed directly adjacent to the probe head 42.

In principle, this hollow space 53 is an end of the gas removal line 52 close to the probe head. The gas is expanded here through the aperture 51 and can then cool the probe head 42, which is preferably constructed from metal (e.g. high-grade steel). By the expansion of the gas, the Joule-Thomson effect causes cooling of the probe head 42. In this context, the gas, which is under high pressure, cools severely on passage through a narrow nozzle (here the aperture), so that the cryoprobe tip (probe head) cools, and freezes the adjacent tissue. Thereafter, the gas can be removed from the hollow space 53 again and therefore from the probe 40 via the gas removal line 52. The gas delivery line 50 mounted eccentrically here could also be arranged, for example, coaxially with the gas removal line 52.

Such cryosurgery apparatuses are envisioned as having diverse possible uses, as shown here operating, for example, by the abovementioned Joule-Thomson effect. Cryosurgical interventions can also be performed by means of liquid nitrogen.

Figure 3:
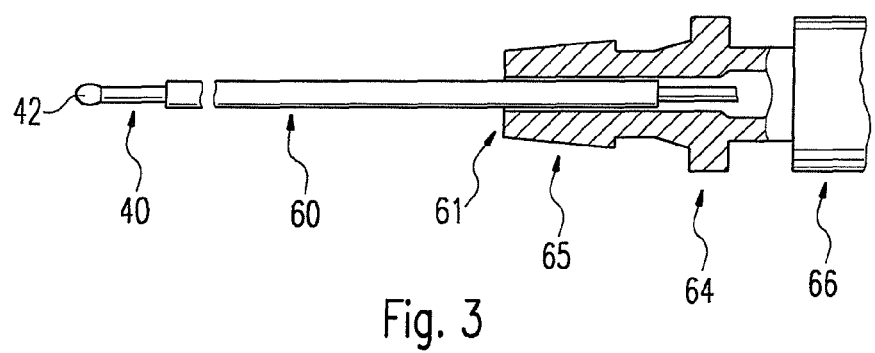
FIG. 3 shows a section of the instrument according to the invention with a diagram of the fixing of a support means to a receiving means.

FIG. 3 shows the probe 40 with support means 60, the proximal end 61 of the support means 60 being fixed in the holding means 65, shown in section, of the receiving means 64. The support means 60 is fixed in the holding means 65 in such a way that the two means cannot be moved relative to one another. Needless to say, the clamping or fixing of the support means 60 in the receiving means 64 should not impede the possibility of moving the probe 40 and support means 60 relative to one another.

Figure 4:
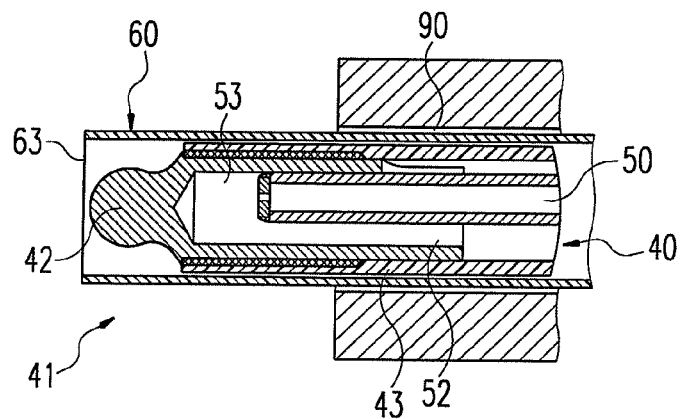
FIG. 4 shows the distal end of the probe, with a support means, guided in a working channel of an endoscope, in section.

FIG. 4 shows the distal end 41 of the probe 40 in section, the support means 60 or here the support tube being pushed over the probe head 42. The support tube 60 is therefore guided in a manner enclosing the probe 40, so that at least the probe head 42 can be received in the support tube 40 and can be released from this again. The working channel 90 of an endoscope in which the probe 40 with the support means 60 is inserted is furthermore shown.

The probe head is preferably—as already explained above—constructed from metal. The probe itself, i.e. the probe body, is preferably constructed from a polyether ketone (PEK), preferably from a polyether ether ketone (PEEK) or plastic of the like. The support means is also preferably constructed from a plastic, e.g. from perfluoro-(ethylene-propylene) plastic (FEP), from polytetrafluoroethylene (PTFE) or a plastic of the like.

Figure 5:
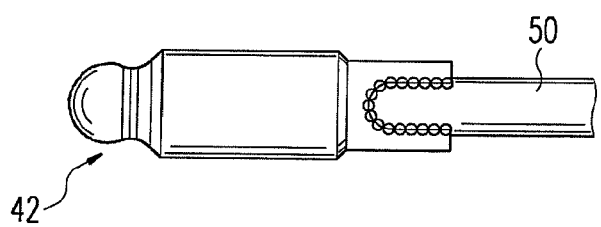
FIG. 5 shows the probe head.

In FIG. 5, the probe head 42 is shown by itself, such as it can then be received in the probe body. It is essentially spherical in design here, and has a roughened surface. A roughened surface has the effect of increasing the surface area, so that deposition (better adhesion) of the tissue on to the probe head 42 is assisted due to the structure. This prevents the biopsy sample from being lost during recovery. The probe head can also have a coating (which, for example, facilitates deposition of the tissue). A polished configuration of the probe head is of course also possible. The spherical form simplifies collection of samples when the cryoprobe is applied laterally to the tissue to be treated.

The probe head here is provided with a type of carrier element integrally with the latter, in order to position the probe via the carrier element and to fix the probe head in this way. The carrier element has an elongated hole at one end, to which the gas delivery line 50 is fixed, e.g. welded, to release tension. The gas delivery line is thus fixed around the periphery of the elongated hole e.g. by laser welding.

Figure 6:
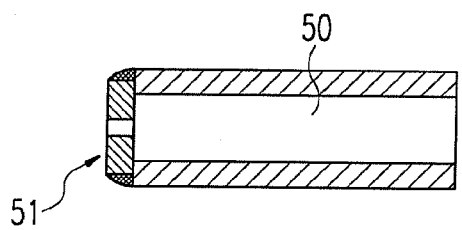
FIG. 6 shows a part of the gas delivery line with an aperture, in section.

FIG. 6 shows the aperture 51 constructed on the end of the gas delivery line close to the probe head. On passage through the hole region, expansion of the gas takes place in such a way that it is cooled and cooling of the probe head 42 therefore takes place.

Figure 7A:
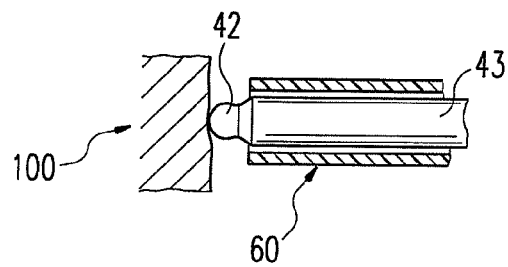
FIG. 7A shows the distal end of the probe, this being positioned on a tissue to be treated.
Figure 7B:
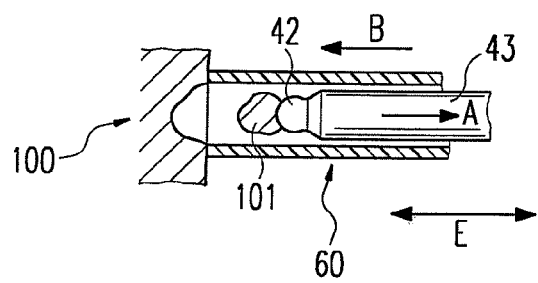
FIG. 7B shows the distal end of the probe, a tissue sample having been removed.

FIG. 7A and 7B show the removal of the tissue sample 101 from the tissue 100 to be treated. Only the probe end with the probe head 42 and support tube 60 are shown here. The endoscope is not shown. In FIG. 7A, the probe head projects out of the support tube (the support means) and is positioned on the tissue 100 to be treated. As soon as a region of the tissue has frozen on the probe head, this region, which finally forms the tissue sample 101, can be separated from the surrounding tissue 100 by moving the probe 40 and support means 60 relative to one another (via the gripping means and pushing means) and dragged into the support tube 60—as shown in FIG. 7B —while at the same time the support tube 60 is positioned on the tissue 100 which surrounds or surrounded the tissue sample 101 and holds back against the pulling force by the probe 40. The arrows indicate any possible directions of movement A, B of the probe 40 and/or support tube 60, respectively, relative to the direction E—the direction in which the probe is extended.

Finally, it is to be noted that it is an essential point of the invention to provide in the cryosurgical instrument a means which supports a tissue, from which a tissue sample is to be removed, in such a way that a pulling force on the surrounding tissue necessary for the removal of the tissue sample is moderated. This is advantageous in particular if the tissue to be treated is suspended in the patient's body in a movable manner and/or is elastic in such a way that it would follow the pulling movement.

The invention claimed is:

1. A cryosurgical instrument comprising:
a probe for guiding a probe head on to a biological tissue to be treated, the probe being mounted in a support means, the probe head being blunt; and
gas conduits for delivery of coolant gas to the probe head, wherein the probe head is operable to collect a tissue sample by cooling a limited region of the tissue by gas delivery and separating the tissue sample from surrounding tissue in a state in which it is frozen on the probe head by means of a pulling force, which acts on the frozen tissue via the probe head, and wherein the support means and probe are configured to position the support means on a tissue surrounding the frozen tissue and to be moved relative to each other in such a way that the support means exerts a counter-force on the surrounding tissue, while the frozen tissue on the probe head is pulled via the probe, such that surrounding tissue can be supported by the support means during separation of the tissue sample, wherein a positioning edge enclosing an opening of the support means on a distal end of the support means is blunt in design for coming into contact with the tissue to be treated.

2. The cryosurgical instrument of claim 1, wherein the probe has a rigid or flexible shaft or catheter and can be guided through an instrument channel of a rigid or flexible endoscope to the tissue to be treated.

3. The cryosurgical instrument of claim 1, further including a gripping means for handling the probe affixed to a proximal end of the probe.

4. The cryosurgical instrument of claim 3, further including a receiving means for receiving a proximal end of the support means, the receiving means and the gripping means being connected to one another such that they are operable to be displaced with respect to one another by means of a coupling unit.

5. The cryosurgical instrument of claim 4, wherein the coupling unit couples a pushing means of the receiving means and a channel region of the gripping means so that the support means and the probe can be moved relative to one another by either a pushing or pulling movement of the gripping means or receiving means.

6. The cryosurgical instrument of claim 1, wherein the gas conduits comprise a gas delivery line running through the probe and a hollow space inside the probe capable of being filled with gas to cool the probe head.

7. The cryosurgical instrument of claim 6, wherein the gas conduits comprise a gas removal line running through the probe, the gas removal line being connected to the hollow space.

8. The cryosurgical instrument of claim 1, wherein the support means encloses the probe in the form of a tube.

9. The cryosurgical instrument of claim 1, wherein at least the probe head can be retracted into the support means to protect the tissue sample frozen on to the probe head.

10. The cryosurgical instrument of claim 1, wherein the support means is operable to be displaced in a direction opposite to the probe such that it provides a counterforce against the surrounding tissue while the tissue sample is separated.

11. A method for separating a tissue sample from surrounding tissue of a biological tissue to be treated with a cryosurgical instrument, the method comprising:
guiding of a probe of the cryosurgical instrument to the tissue to be treated;
positioning of a probe head of the probe on the tissue to be treated, the probe head being blunt;
delivering coolant gas via gas conduits running through the probe to the probe head to cool the probe head such that the tissue sample is cooled and freezes on to the probe head;
displacing a support means surrounding the probe relative to the probe in such a way that the tissue sample is separated from the surrounding tissue by means of a pulling force, which acts on the frozen tissue via the probe head, while the surrounding tissue is supported by means of the support means which exerts a counterforce on the surrounding tissue via a blunt positioning edge on a distal end of the support means; and
recovering the tissue sample.

12. The method of claim 11, wherein the probe has a rigid or flexible shaft or catheter and the guiding step further comprises guiding the probe through a working channel of a rigid or flexible endoscope to the tissue to be treated.

13. The method of claim 11, wherein the displacing step comprises pushing or pulling movement of a receiving means attached to the support means or a gripping means attached to the probe.

14. The method of claim 11, wherein during the displacing step, the support means is displaced in a direction opposite to a direction of movement of the probe such that the support means provides a counterforce against the surrounding tissue while the tissue sample is separated.

15. The method of claim 11, wherein the recovering step comprises retracting the probe head into the support means.

16. An endoscopic tissue biopsy instrument comprising:
a support structure positionable in a working channel of an endoscope; and
a probe displaced within the support structure operable to cryosurgically biopsy a tissue sample by delivery of coolant gas to a probe head, the probe head being blunt, such that of the probe such that after the delivery of coolant gas to the probe head is complete, the probe is operable to be displaced relative to the support structure such that the support structure presses against tissue surrounding the tissue sample and provides counterforce via a blunt positioning edge enclosing an opening of the support structure on a distal end of the support structure, while the tissue sample is separated by means of a pulling force, which acts on the tissue sample via the probe head.

17. The endoscopic tissue biopsy instrument of claim 16, further including gas delivery and removal lines running through the probe to a hollow space within the probe operable to be filled with coolant gas to cool the probe head.

18. The endoscopic tissue biopsy instrument of claim 16, further including a gripping structure affixed to a proximal end of the probe and a receiving structure affixed to a proximal end of the support structure, wherein the receiving structure is interlocked to a channel region of the gripping structure such that displacement of the gripping structure relative to the receiving structure causes displacement of the probe relative to the support structure.

19. The endoscopic tissue biopsy instrument of claim 16, wherein the probe can be withdrawn into the support structure to protect the tissue sample frozen on to the probe head.

* * * * *